United States Patent [19]

Saunders et al.

[11] Patent Number: 4,718,414
[45] Date of Patent: Jan. 12, 1988

[54] INSTRUMENT FOR ELBOW SURFACE REPLACEMENT ARTHROPLASTY

[75] Inventors: Gerald A. B. Saunders, Sydenham; Charles Sorbie, Kingston, both of Canada

[73] Assignee: Queen's University at Kingston, Kingston, Canada

[21] Appl. No.: 894,214

[22] Filed: Aug. 7, 1986

Related U.S. Application Data

[63] Continuation of Ser. No. 730,931, May 6, 1985, Pat. No. 4,624,250, Continuation-in-part of Ser. No. 507,378, Jun. 24, 1983, abandoned.

[51] Int. Cl.⁴ ............................................. A61F 5/04
[52] U.S. Cl. ........................ 128/92 VY; 128/92 VW; 623/20
[58] Field of Search .......... 128/92 VY, 92 V, 92 VV, 128/92 VW, 92 VD, 303 R; 623/20

[56] References Cited

U.S. PATENT DOCUMENTS

| | | | |
|---|---|---|---|
| 3,547,115 | 12/1970 | Stevens | 128/92 VW |
| 3,868,730 | 3/1975 | Kaufer et al. | 128/92 V |
| 4,100,626 | 7/1978 | White | 128/92 V |
| 4,242,758 | 1/1981 | Amis et al. | 128/92 VW |
| 4,378,607 | 4/1983 | Wadsworth | 128/92 VY |
| 4,624,250 | 11/1986 | Saunders et al. | 623/20 |

Primary Examiner—C. Fred Rosenbaum
Assistant Examiner—C. W. Shedd
Attorney, Agent, or Firm—Richard J. Hicks

[57] ABSTRACT

A bone cutting device for precision elbow surface replacement arthroplasty and osteotomy is described. A humeral clamping device is provided with an outrigger to hold the ulna in preselected and rigid relation to the humerus. A bond cutting tool such as a burr is inserted into a selected guide sleeve mounted for oscillatory arcuate movement on the medial side of the clamping device, so as to precisely prepare the humerus. The humeral guide sleeve is removed and replaced with a slightly longer second sleeve which provides the precise spacing required to prepare the ulna in similar manner. A planar radial cutting guide may be mounted on the lateral side of the clamping device, to guide a planar oscillating saw used to prepare the proximal end of the radius.

4 Claims, 15 Drawing Figures

INSTRUMENT FOR ELBOW SURFACE REPLACEMENT ARTHROPLASTY

CROSS REFERENCE TO RELATED APPLICATIONS

This application is a continuation of U.S. patent application Ser. No. 730,931 filed May 6, 1985, now U.S. Pat. No. 4,624,250 which in turn is a continuation-in-part of our earlier filed U.S. patent application Ser. No. 507,378 filed June 24, 1983, now abandoned, the disclosure of which is incorporated herein by reference.

FIELD OF INVENTION

This invention relates to an orthopaedic joint clamping and bone cutting device. More particularly this invention relates to a bone cutting device for precision elbow surface replacement arthroplasty and osteotomy.

BACKGROUND OF INVENTION

The complex kinematics, anatomical features and load distribution on an elbow are such that surgical replacement thereof is not simple. Simple constrained and semi-constrained cemented replacements for the elbow joint have proved to be generally unsatisfactory as they do not provide sufficient range of motion and, due to the unnatural stresses placed on the musculature, ligaments and tendons, premature loosening often within a year or two of placement frequently occurs. Loosening is usually accompanied by pain and discomfort and over a period of time distortion of the natural function of the joint may occur. The use of unconstrained resurfacing prostheses, such as those described in the aforesaid application Ser. No. 507,378 and in U.S. Pat. No. 4,242,758 issued Jan. 6, 1981 to Amis et al, appears to offer the potential, by reproduction of normal joint geometry and restoration of ligament balance, to recreate relatively normal kinematics and load bearing and to provide relief of pain. Such prostheses are now generally using the relatively recently developed porous metal coating technique so as to promote bone ingrowth, and this technique precludes the use of cements to secure the prosthesis to the bone or to compensate for cutting inaccuracies. It is now necessary to ensure accurate resection of the bone ends to within a tolerance of 1 mm or better. Such accuracies are not possible using commonly available jigs or with hand held saws or other cutting tools such as router tools.

OBJECT OF INVENTION

It is therefore an object of the present invention to provide a novel surgical method to hold an elbow joint in a preselected position so as to accurately resect the humeral, ulna and radial bones without moving the joint between cuts. The cuts are precisely positioned to receive a resurfacing prosthesis, of one of five preselected standard sizes, such as that described in our application for U.S. Letters Patent entitled "Elbow Prosthesis" Ser. No. 730,814 filed May 6, 1985.

BRIEF STATEMENT OF INVENTION

By one aspect of the invention there is provided a method for surgically implanting an elbow prosthesis comprising:
(a) exposing medial and lateral epicondyles of an elbow to be replaced;
(b) removing a crown from each of said medial and lateral epicondyles so as to provide flattened epicondylar plateaus;
(c) determining a geometric trochleal centre and a geometric capitellum centre on respective ones of said epicondylar plateaus, and drilling pilot holes thereat;
(d) mounting a width-adjustable humeral clamp, provided with a pair of mounting pins, on said elbow by inserting said pins into respective ones of said pilot holes, adjusting the width of said clamp and securing in a selected orientation by insertion of at least one lateral locking pin;
(e) mounting one end of a longitudinally extending ulna fixation assembly on said humeral clamp perpendicularly thereto; said ulna fixation assembly having an adjustable crosshead assembly at the free end thereof, coronoid arms extending from each end of said crosshead assembly and an olecranon bracket extending intermediate the ends of said crosshead and angularly adjustable so that a pin extending through the free end thereof into the olecranon is substantially parallel to the axis of said ulna;
(f) securing said ulna and humerus at an inclined angle of about 135 degrees with strap means between the distal end of the ulna and the proximal end of the humerus;
(g) securing said pin extending through the olecranon bracket in a plane parallel the axis of said ulna;
(h) mounting a selected humeral cutting cam on said humeral clamp on the medial side thereof;
(i) inserting a cutting means through said cutting cam and shaping the trochleal and capitelum portions of the distal end of said humerus therewith;
(j) replacing said humeral cutting cam and cutting means with a selected ulna cutting arc template;
(k) inserting said cutting means through said cutting arc template and shaping the proximal end of said ulna therewith;
(l) mounting a radial cutting gauge on the lateral side of the humeral clamp and resecting the proximal end of the radius;
(m) removing said humeral clamp from said elbow;
(n) mounting a radius prosthesis on said resected radius from the lateral side of the elbow;
(o) slidingly inserting a humeral prosthesis on said humerus from the medial side;
(p) slidingly inserting an ulna prosthesis on said prepared ulna from the medial side;
(q) replacing said medial and lateral epicondyles; and
(r) closing both medial and lateral wound sites.

DETAILED DESCRIPTION OF PREFERRED EMBODIMENTS

In the copending application Ser. No. 730,814 filed May 6, 1985, a novel humeral resurfacing prosthesis which substantially replicates the distal end of a humerus is described. While it was first thought that the use of external anatomical landmarks, such as the epicondyles, would provide the means to establish the radial centre for the convex semi-circular cut at the distal humerus necessary to receive the prosthesis, this approach was discarded as it was found that the axis (or C-line) of the trochlea and capitellum, which is substantially a straight line, is in fact at an angle of about 2°–3° to the transepicondylar line (TEL). Instead use is made of the curved surface of the trochlea and capitellum. An incision is made first on the medial side of the elbow and, after drilling a pilot hole in the centre of the medial epicondyle, the epicondylar crown is removed (for later replacement and securement by a screw inserted into the pilot hole). A series of differently sized semicircular trochlear templates 10 are placed on the now flattened medial epicondylar plateau to establish, by a "best fit" approach, the geometric centre of the medial aspect of the trochlear, which is then marked and a pilot hole drilled thereat. After making an incision and exposing the lateral side the procedure is repeated with a series of capitellum templates 101, which establishes the geometric centre of the capitellum.

Figure 1:
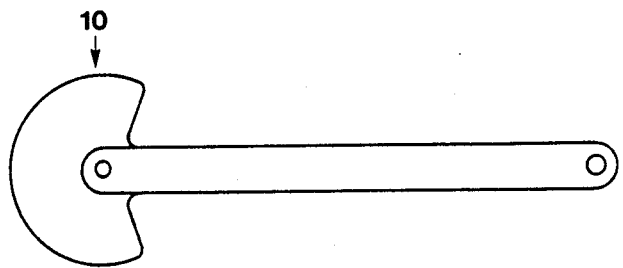
FIG. 1 is a plan view of a trochlear template.
Figure 2:
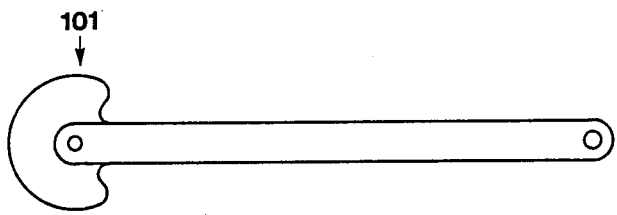
FIG. 2 is a plan view of a capitellum template.
Figure 3:
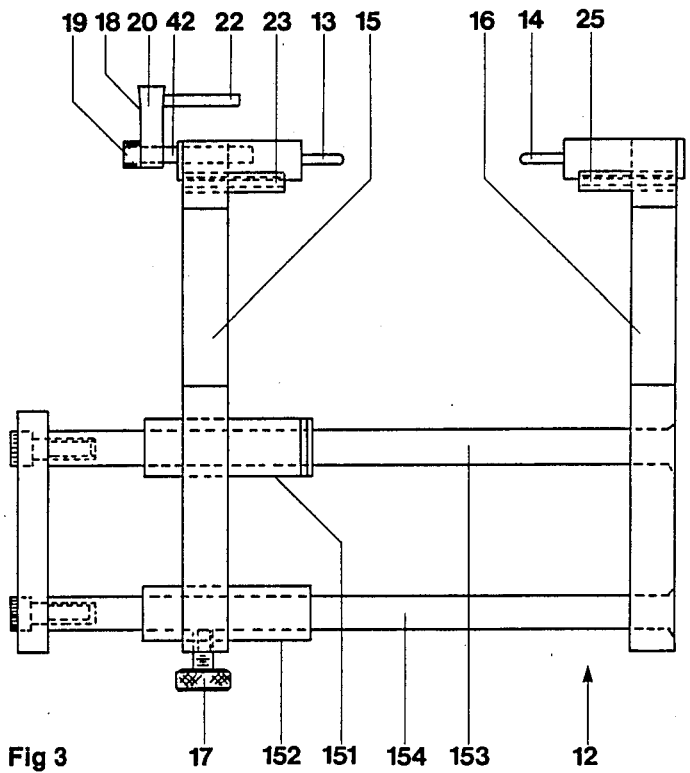
FIG. 3 is a front view of a humeral clamp according to the invention.
Figure 4:
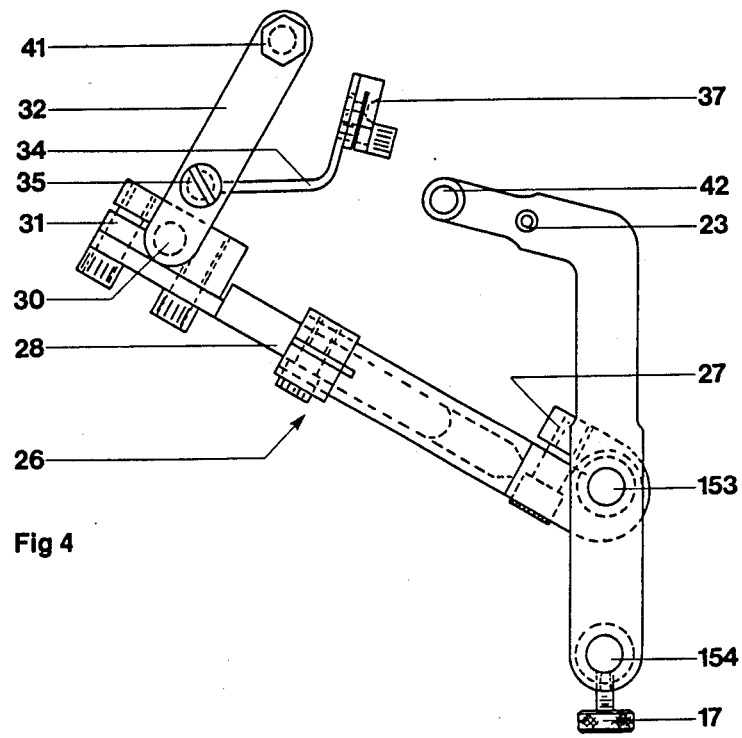
FIG. 4 is a side view of a humeral clamp of FIG. 3 with an ulna outrigger installed.
Figure 5:
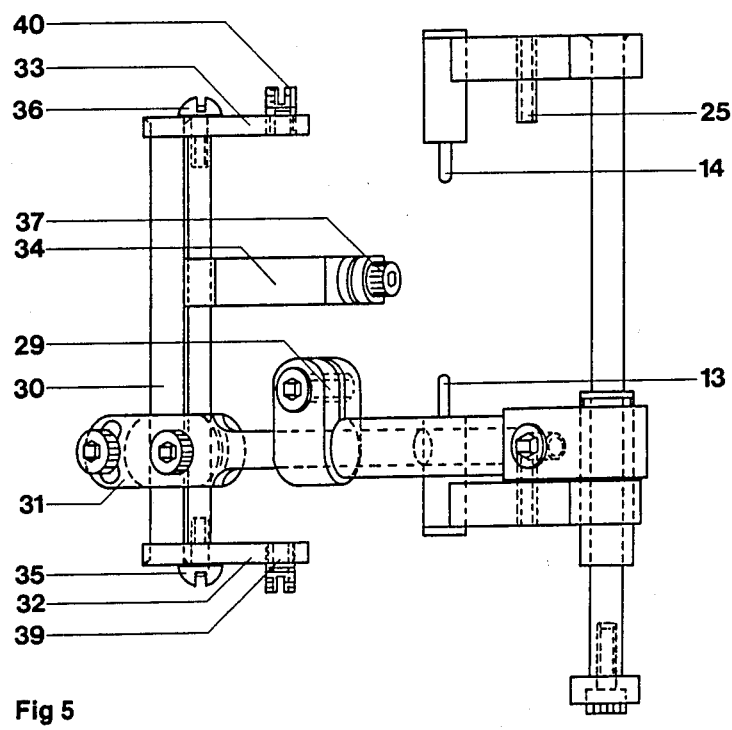
FIG. 5 is a bottom view of the device of FIG. 4
Figure 6:
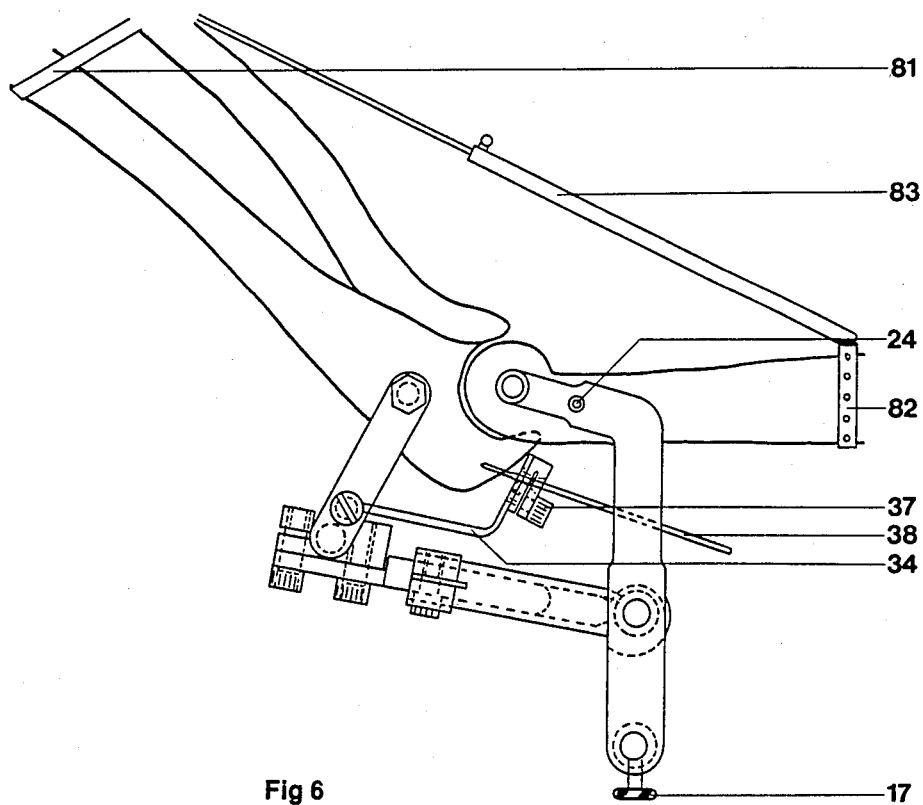
FIG. 6 is a diagramatic sketch of the device of FIG. 4, in position on an elbow.
Figure 7:
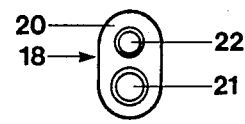
FIG. 7 is a side view of a humeral cutting cam.

A U-shaped width-adjustable humeral clamp 12 with locating pins 13,14 at the ends of the areas thereof, is placed on the humerus and the pins located in the respective trochlea (medial) and capitellum (lateral) pilot holes. Once the pins are located, the arms 15,16 of the clamp are adjusted towards each other by sliding integral sleeves 151,152 along respective guide rods 153,154 and locked in place by clamping screw 17 thereby securely locating the clamp and yet still allowing it to be rotated about the C-line axis of the humerus. A humeral cutting cam 18 (FIG. 7) of selected length is axially mounted on shouldered guide pin 42 at the end of the medial arm 15 of the clamp and rotatably secured by means of locking nut 19 as seen in FIG. 3. The cam 18 comprises a body 20, having a circular hole 21 therethrough adjacent one end, adapted to be mounted on pine 42 which is in turn arranged to receive locking screw 19, and about which body 20 may be arcuately oscillated, and a hollow guide 22 axially parallel to and spaced a selected distance from hole 21. Guide 22 is adapted to receive a rotatable burr (not shown) generally about ⅜" in diameter. The burr may be rotated by any conventional power or air tool normally found in an operating theatre. The cam with the burr in place is oscillated back and forth to ensure that the correct cutting arc has been established. Once the surgeon is satisfied with the cutting arc, cam 18 may be removed if desired. A 3/32" Steinman pin 24 is then inserted through hole 23 in the clamp 12 and screwed into the underlying prepared surface of the medial epicondyle. This prevents the clamp from rotating on its axis. A similar Steinman pin may be inserted through complementary pilot hole 25 on the lateral side to further assist in rigidly mounting the clamp. The ulna fixation assembly 26 is next mounted on the humeral clamp by means of U-clamp 27. The ulna fixation assembly 26 comprises a telescopically expandable arm 28, lockable at any selected length by U-clamp 29. A crosshead 30 is adjustably and clampingly mounted at the end of arm 28 by means of clamp 31 intermediate the ends thereof. Coronoid arms 32, 33 extend substantially perpendicularly to arm 28 and to crosshead 30 at opposite ends thereof and angularly adjustable relative thereto. Intermediate the ends of crosslead 30 there is provided an olecranon bracket 34 which may be locked at any desired angle to arms 32, 33 by means of locking screws 35, 36. The olecranon bracket 34 is adjusted so that the adjustable pin clamp 37 lies adjacent the olecranon, and a threaded Steinman pin 38 may be inserted through clamp 37 and drilled not more than about 1 cm into the olecranon so that pin 38 is substantially parallel to the longitudinal axis of the ulna. With the elbow flexed at about 45°, and held at that angle by a rigid, telescopically adjustable bracket 83 and wrist 81 and humeral straps the linked, parallel coronoid bracket arms 32, 33 are adjusted to lie adjacent the coronoid areas on their respective side of the ulna. A 5/32" threaded Steinman pin may now be inserted through medial guide hole 39, drilled through the ulna and into the guide hole 40 on the lateral side. When all the pins are in place and the surgeon is satisfied with the orientation of the ulna and radius relative to the humerus, the adjustment 26,27,31,35,36,37,41, are locked in place to hold the ulna and humerus in the selected orientation.

A selected humeral cutting cam 18 is then remounted, if previously removed, on pin 42 and secured by nut 19, preparatory to making the humeral cuts. A selected rotatable burr, preferably provided with a depth control gauge (not shown) inserted into hole 22 and may then be actuated by any conventional air or electric power source. Once inserted, it is preferable to drill to full depth at each extreme of arc. Subsequently, the cam may be moved in either direction, but generally counterclockwise, to remove the remainder of the bone in the trochleal cutting arc, cutting to a depth of about 1 cm at a time and spraying the burr continuously with a sterile saline solution to prevent overheating of the bone and to wash away debris. Once the trochleal surface has been removed, and it is here emphasized that the present protocol is designed to remove a minimum of bone stock, the depth control gauge is adjusted to the depth required to cut the capitellum portion, and the capitellum is cut in similar manner to the trochlea. Without removing the clamp from the humerus and ulna, the humeral cutting cam is removed and replaced with an ulna cutting cam which is similar in shape to humeral cutting cam 18, but with a slightly larger, and predetermined selected cutting radius. It will be appreciated that, according to our copending application "Elbow Prosthesis" filed May 6, 1985, Ser. No. 730,814, it has been possible to generate 5 standard sizes of humeral prostheses to fit 95%, of the population. Complementary ulna and radial prostheses of varying thickness are also available, so that the surgeon may select the most suitably sized humeral prosthesis and match it with a similarly standardized ulna or radial prosthesis. Thus the clearance required between the humeral and ulna prepared bone surfaces is readily predetermined, and the exact cutting radius for the ulna cutting cam selected. Once selected, positioned and locked in place by nut 19, the depth gauge is set and cutting of the ulna proceeds in a similar manner to the humeral cut, it being perferred to rotate the ulna cam in a clockwise manner.

The ulna cam is then removed and a flat radius cutting gauge (not shown) is locked in appropriate orientation on the humeral clamp on the lateral side 16 thereof. Using the flat surface thereof as a guide for an orthopaedic oscillating saw (not shown) the head of the radius is resected.

Any excess bone or cartilage tissue, which might interfere with prosthesis implantation may be trimmed away, from the medial side, by means of selected profile tools and osteotones. Generally such tools may be guided by means of guides (not shown) mounted on the humeral frame. The frame can then be dismounted from the ulna and humerus.

Figure 8:
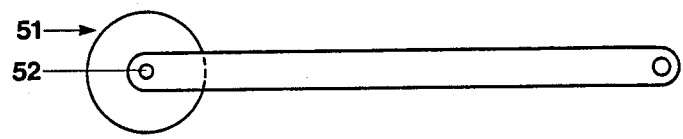
FIG. 8 is a plan view of a radius gauge.
Figure 9:
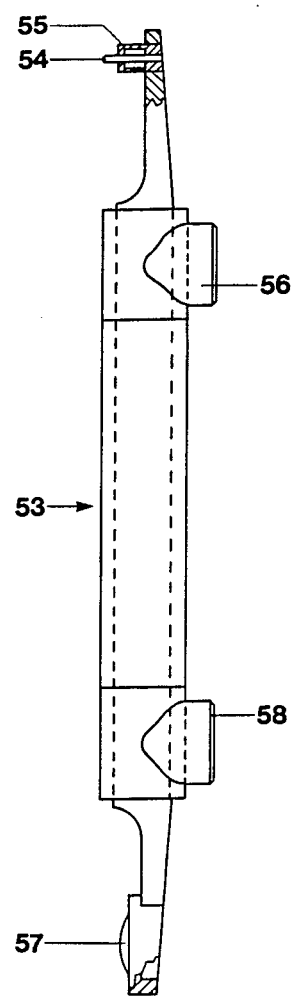
FIG. 9 is a side view of a radius centre pin cutter.
Figure 10:
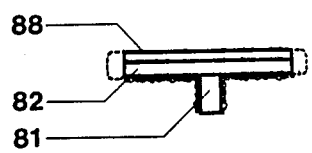
FIG. 10 is a side view of a radial prosthesis.
Figure 11:
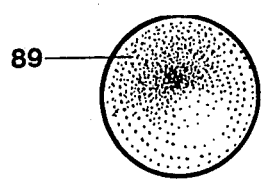
FIG. 11 is a plan view of the prosthesis of FIG. 10.

The arm may then be rotated to the lateral side and a radius gauge 51 (FIG. 8) is selected, from a sized set thereof, which most closely corresponds in diameter to that of the radius and placed over the squarely prepared proximal end of the radius. A marker probe is inserted through hole 52 and used to mark the centre of the radius. The gauge 51 is then removed and replaced by radius centre pin cutter 53 (FIG. 9) the centering pin 54 of which is inserted into the marked centre of the radius. The cutter 55 is tapped home by means of a small osteotone which is struck against strike 56. The cutter 53 is then rotated axially about pin 54, in an arc of about 45° in each direction and then removed, thus removing a cylindrical core of bone from the radius. The radial prosthesis 88 (FIGS. 10, 11) is then inserted with the stem 81 projecting into the cored hole formed in the radius. The prosthesis is tapped into position by placing the convexly contoured surface 57 to tool 53 over the concave surface 89 of prosthesis 88 and striking striker 58 with a small osteotone.

Figure 12:
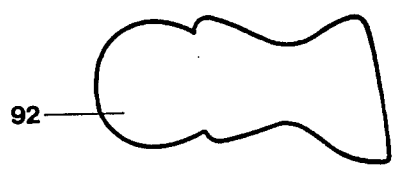
FIG. 12 is a front view of a humeral prosthesis
Figure 13:
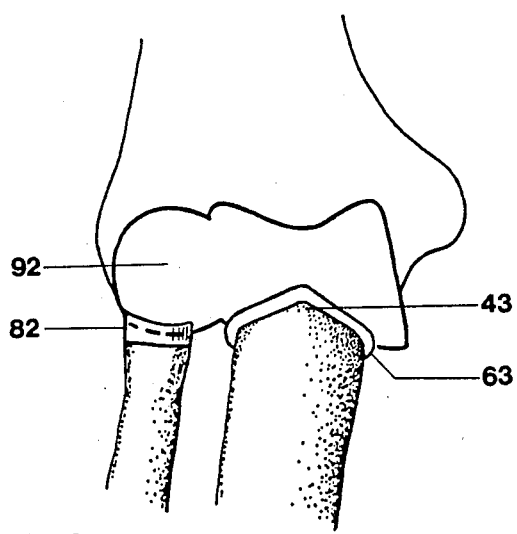
FIG. 13 is a sketch of an anterior view of a right elbow including the humeral, ulnar and radial prosthesis of the present invention.
Figure 14:
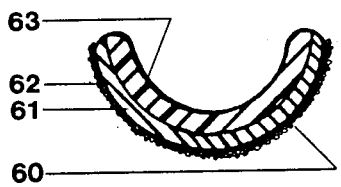
FIG. 14 is a medial view of an ulna prosthesis.
Figure 15:
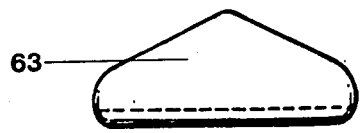
FIG. 15 is an anterior view of the prosthesis of FIG. 14.

The arm is again rotated to the medial side and the humeral prosthesis 92 (FIG. 12) is inserted into position, as shown in FIG. 13, tapping if required to achieve the desired position and taking care not to disturb the radial prosthesis. The ulna prosthesis 63 (FIGS. 14, 15) is then inserted, also from the medial side, and its position adjusted as necessary. Locating pins, if used, are pressed into the underlying ulna bone. Using a bone screw inserted into the predrilled pilot hole, the medial epicondyle is replaced, oriented and secured in place, and after checking to ensure alignment and free movement, the medial and lateral wounds may be closed.

We claim:

1. A method for surgically implanting an elbow prosthesis comprising:
(a) exposing medial and lateral epicondyles of an elbow to be replaced;
(b) removing a crown from each of said medial and lateral epicondyles so as to provide flattened epicondylar plateaus;
(c) determining a geometric trochleal centre and a geometric capitellum centre on respective ones of said epicondylar plateaus, and drilling pilot holes thereat;
(d) mounting a width-adjustable humeral clamp, provided with a pair of mounting pins, on said elbow by inserting said pins into respective ones of said pilot holes, adjusting the width of said clamp and securing in a selected orientation by insertion of at least one lateral locking pin;
(e) mounting one end of a longitudinally extending ulna fixation assembly on said humeral clamp perpendicularly thereto; said ulna fixation assembly having an adjustable crosshead assembly at the free end thereof, coronoid arms extending from each end of said crosshead assembly and an olecranon bracket extending intermediate the ends of said crosshead and angularly adjustable so that a pin extending through the free end thereof into the olecranon is substantially parallel to the axis of said ulna;
(f) securing said ulna and humerus at an inclined angle of about 135 degrees with strap means between the distal end of the ulna and the proximal end of the humerus;
(g) securing said pin extending through the olecranon bracket in a plane parallel the axis of said ulna;
(h) mounting a selected humeral cutting cam on said humeral clamp on the medial side thereof;
(i) inserting a cutting means through said cutting cam and shaping the trochleal and capitelum portions of the distal end of said humerus therewith;
(j) replacing said humeral cutting cam and cutting means with a selected ulna cutting arc template;
(k) inserting said cutting means through said cutting arc template and shaping the proximal end of said ulna therewith;
(l) mounting a radial cutting gauge on the lateral side of the humeral clamp and resecting the proximal end of the radius;
(m) removing said humeral clamp from said elbow;
(n) mounting a radius prosthesis on said resected radius from the lateral side of the elbow;
(o) slidingly inserting a humeral prosthesis on said prepared humerus from the medial side;
(p) slidingly inserting an ulna prosthesis on said prepared ulna from the medial side;
(q) replacing said medial and lateral epicondyles; and
(r) closing both medial and lateral wound sites.

2. A method as claimed in claim 1 wherein said geometric trochleal and capitellum centres are determined by means of templates of selected size.

3. A method as claimed in claim 1 wherein said proximal end of said ulna and said distal end of said humerus are shaped using a rotatable burr inserted through said cutting cam.

4. A method as claimed in claim 2 wherein said radius is resected with an oscillating cutting means guided by said cutting gauge.

* * * * *